(12) United States Patent
Liu et al.

(10) Patent No.: US 12,228,562 B2
(45) Date of Patent: Feb. 18, 2025

(54) METHOD FOR ASSESSING SOIL HEALTH OF CULTIVATED LAND

(71) Applicant: Institute of Mountain Hazards and Environment, Chinese Academy of Sciences, Chengdu (CN)

(72) Inventors: Gangcai Liu, Chengdu (CN); Kai Hu, Chengdu (CN); Xuan Wang, Chengdu (CN)

(73) Assignee: Institute of Mountain Hazards and Environment, Chinese Academy of Sciences, Chengdu (CN)

( * ) Notice: Subject to any disclaimer, the term of this patent is extended or adjusted under 35 U.S.C. 154(b) by 674 days.

(21) Appl. No.: 17/530,324

(22) Filed: Nov. 18, 2021

(65) Prior Publication Data
US 2022/0308036 A1 Sep. 29, 2022

(30) Foreign Application Priority Data
Mar. 27, 2021 (CN) .......................... 202110328796.3

(51) Int. Cl.
*G01N 33/24* (2006.01)
(52) U.S. Cl.
CPC ........... *G01N 33/24* (2013.01); *G01N 33/243* (2024.05); *G01N 33/245* (2024.05)
(58) Field of Classification Search
None
See application file for complete search history.

(56) References Cited

U.S. PATENT DOCUMENTS

| | | | | |
|---|---|---|---|---|
| 2016/0073573 | A1* | 3/2016 | Ethington | G06Q 10/06 705/7.36 |
| 2020/0271636 | A1* | 8/2020 | Hartman | G16B 20/00 |

OTHER PUBLICATIONS

Liu Guangsong, Soil Physical and Chemical Analysis & Description of Soil Profiles. Standards Press of China. 1996. pp. 123-167. China.
Wang Xingchun, Yang Zhirong, Wang Min, Li Wei, Li Shengcai, High-Throughput Sequencing Technology and Its Application. China Biotechnology. 2012. vol. 32 (01). pp. 109-114. China.
(Continued)

*Primary Examiner* — Roy Y Yi
(74) *Attorney, Agent, or Firm* — Simpson & Simpson, PLLC (57) ABSTRACT

The present disclosure discloses a method for assessing soil health of cultivated land, which adopts "three sets of dual index assessment systems", that is an index system for current soil function and a healthy soil function required by crops, an index system for current soil nutrition and healthy soil nutrition required by crops, and an index system for current crop output of cultivated land and a crop output expected by cultivated land users or owners. The method solves the shortcomings of the existing assessment systems that the existing soil health assessment index system has no hierarchy and applicability. This method includes using deviating degree of ratio R e.g., the index current value C/index health value E of measured dual index from 1 as well as it is simple, and the assessment result may directly determine the indicators or factors that can be used for guiding soil improvement and conservation.

10 Claims, 1 Drawing Sheet

(56) References Cited

OTHER PUBLICATIONS

Bi Chun-Juan, Chen Zhen-Lou, Wang Jun and Zhou Dong. Quantitative Assessment of Soil Health Under Different Planting Patterns and Soil Types. Pedosphere. 2013. vol. 23(2). p. 194-204. Published by Elsevier B.V. and Science Press. China.

Bünemann, Else & Bongiorno, Giulia & Bai, Zhanguo & Creamer, Rachel & Deyn, G.B. & R. G. M., Goede & Fleskens, Luuk & Geissen, Violette & Kuyper, Thom & Mäder, Paul & Pulleman, Mirjam & Sukkel, W. & Groenigen, Jan & Brussaard, Lijbert. Soil quality—A critical review. Soil Biology and Biochemistry. May 2018. p. 105-125. vol. 120. Published by Elsevier B.V.

Cai Xiaoxi, Wu Jinzhuo. Research Progress on the Assessment of Forest Soil Health. Forest Engineering, Mar. 2015. vol. 31(2). Northeast Forestry University. Harbin, China.

Cao Hongyu, Gao Guanglei, Ding Guodong, Zhao Yuanyuan, Wang Yue, Li Xu. Soil Health Assessment in Typical Forest of Mulan Paddock. Journal of Shanxi Agricultural University Natural Science Edition. 2017. p. 713-718. vol. 37, ISSN 1671-8151. Published by Shanxi Agricultural University, Shanxi, China.

Sumita Chandel, D Tripathi, Ridham Kakar. Soil Health Assessment Under Protected Cultivation of Vegetable Crops in North West Himalayas. Journal of Environmental Biology. Jan. 2017. p. 97-103. vol.38. Published by Triveni Enterprises. Lucknow(India).

Pang Xue-Yong, Liu Qing, Liu Shi-Quan, Wu Yan, Lin Bo, He Hai, Zhang Zong-Jin. Changes of Soil Fertility Quality Properties Under Subalpine Spruce Plantation in Western Sichuan. ACTA Ecologica Sinica. Feb. 2004. p. 261-267. vol. 24(2). Published by Elsevier B.V.

Gayatri Sahu, Samanyita Mohanty. Soil Health and Sustainability. Current Research in Soil Science. May 2021. p. 29-45. Published by AkiNik Publications. New Delhi, India.

Avanthi Deshani Igalavithana, Sang Soo Lee, Nabeel Khan Niazi, Young-Han Lee, Kye Hoon Kim , Jeong-Hun Park, Deok Hyun Moon, and Yong Sik Ok. Assessment of Soil Health in Urban Agriculture: Soil Enzymes and Microbial Properties. Sustainability. Feb. 2017. 9,310. Published by MDPI, Basel, Switzerland.

Jing Ma. Study on Assessment of Soil Health and Biological Control Techniques for Pinus tabulaeformis Plantation. Feb. 2017. College of Forestry, Inner Mongolia Agricultural University, Huhhot, 010018, China.

K.L. Nelson, D.H. Lynch, G. Boiteau. Assessment of changes in soil health throughout organic potato rotation sequences. Agriculture, Ecosystems and Environment. Feb. 2009. pp. 220-228. Published by Elsevier B.V.

Sambo Pheapa, Clara Lefevreb, Alexis Thoumazeauc, Vira Lenge, Stéphane Boulakiab,Ra Koye, Lyda Hoka, Pascal Lienhardb, Alain Braumanc, Florent Tivetb. Multi-functional Assessment of soil health under Conservation Agriculture in Cambodia. Soil & Tillage Research. Aug. 2019. vol. 194. Published by Elsevier B.V.

Ren Lina, Wang Haiyan, Ding Guodong, Gao Guanglei, Sun Jia, Liu Ling, Yang Xiaojuan, Li Wenye. Research Advances on Assessment of Soil Health of Forest Ecosystem. World Forestry Research. Oct. 2011. vol. 24(5). Published by Shi Jie Lin Ye Yan Jiu Bian Ji Bu. China.

Oshri Rinot, Guy J. Levy, Yosef Steinberger, Tal Svoray, Gil Eshel. Soil Health Assessment: A Critical Review of Current Methodologies and a Proposed New Approach. Science of the Total Environment. Jan. 2019. pp. 1484-1491. vol. 648. Published by Elsevier B.V.

Sheng Feng. Introduction and Application of Cornell Soil Health Assessment. Chinese Journal of Soil Science. Tu Rang Tong Bao Bian Ji Bu. Dec. 2014. pp. 1289-1296vol. 45(6). China.

Xiaoyan Tang, Rui Li, Y. Zheng, Murray B. McBride. Health Assessment of Nickel-Contaminated Soils Linked to Chemical and Biological Characteristics. Soil Biology & Biochemistry. May 2019. pp. 614-623. vol. 83. Published by Elsevier B.V.

Tao Baoxian, Zhang Jinchi, Lin Jie, Zhang Bo, Cui Zhihua, Kong Yuguang, Yu Yuanchun. Soil Quality Assessment of Different Forest Stands in the Hilly Region of Southern Jiangsu Province. Journal of Nanjing Forestry University (Natural Science Edition). Nov. 2009. vol. 33(6). China.

Yang Xiao-Juan, Wang Hai-Yan, Ren Li-Na, Yu Yang, Liu Ling. Forest Soil Health Assessment in China: A Review. Chinese Journal of Soil Science. Aug. 2012. vol. 43(4). Published by Tu Rang Tong Bao Bian Ji Bu.China.

Yu Fa-Zhan, Zhang Zhong-Qi, Chen Long-Qian, Shen Zheng-Ping. Soil Characteristics and Health Assessment for Different Forest Vegetation In Lushan. Resources and Environment in the Yangtze Basin. Jul. 2016. vol. 25(7). Published by Chang Jiang Liu Yu Zi Yuan Yu Huan Jing Bian Ji Bu. China.

Zhang Min, Sheng Feng. Application of Multilevel Fuzzy Comprehensive Evaluation Method in Soil Health Assessment. Journal of Northern Agriculture. 2017. pp. 92-96. vol. 45(6). China.

Zhao Rui, Wu Ke-Ning, Liu Ya-Nan, Feng Zhe. Soil Health Evaluation at a County Level Based on Soil Ecosystem Service Function. Chinese Journal of Soil Science. Apr. 2020. vol. 51(2). Published by Tu Rang Tong Bao Bian Ji Bu. China.

Liu Guangsong, Soil Physical and Chemical Analysis & Description of Soil Profiles. (Beijing, Standards Press of China, 1996).

Wang Xingchun, Yang Zhirong, Wang Min, Li Wei, Li Shengcai, High-Throughput Sequencing Technology and Its Application (China Biotechnology, 2012, 32 (01): 109-114).

\* cited by examiner

METHOD FOR ASSESSING SOIL HEALTH OF CULTIVATED LAND

CROSS REFERENCE TO RELATED APPLICATION(S)

This patent application claims the benefit and priority of Chinese Patent Application No. 202110328796.3 filed on Mar. 27, 2021, the disclosure of which is incorporated by reference herein in its entirety as part of the present application.

TECHNICAL FIELD

The present disclosure relates to soil assessment, and more particularly to a method for generating a soil health assessment for cultivated land.

BACKGROUND ART

"Soil health" was proposed by British ecologist Balfour in his book "The Soil of Life" in 1947 (translated by Ma Jing, 2017). Different scholars have different definitions of soil health. Some researchers believed that soil health refers to comprehensive soil management measures using a combination of physical, chemical, and biological methods, in order to make the plant development achieve long-term sustainability on the premise of preventing the negative impact of production on the environment to the greatest extent. Other conventional research theorized that the criterion of "soil health" is to produce animal and plant products that have health benefits to the human body and can improve water and air quality, resist pollutants, and promote the ability of plants, animals, microorganisms and human health. Some conventional theory finds that soil health means that the soil is in a dynamic process with a good structural and functional state, can provide stable and sustainable biological productivity, maintain ecological balance, promote biological health, and will not degenerate and cause harm to the environment, and that the soil health is the ability of the soil, to sustainably maintain biological productivity, promote the quality of air and water environment, and the health of plants, animals, and humans. The Food and Agriculture Organization of the United Nations (FAO) defined "soil health" as "soil as a living system having the ability to maintain its functions" in 2011. Forest soil health can be defined as: it is the ability of forest soil to promote forest vegetation production and maintain forest ecosystem functions. In general, most researchers currently believe that "soil health" is synonymous with "soil quality."

An assessment index system of soil health generally includes three performance indicators of soil: physics, chemistry, and biology. However, the assessment indicators used by different researchers are significantly different. Modern researchers have selected 8 indicators that include, soil bulk density, mass water content, pH, physical clay being less than 1 mm, and the presence of organic matter, total nitrogen, rapidly available potassium, and available phosphorus to assess the soil health of typical forest stands in Mulan Paddock. Researchers have selected 14 indicators, including the thickness of the litter layer, to assess the soil health status of different forests in Lushan Mountain. Other research indicated a belief that soil health assessment may include soil morphological indicators such as soil thickness. Some investigators further believe that soil pollutants such as heavy metals may also be an indicator of soil health assessment. Recently, some researchers proposed that the soil health assessment may include indicators of soil ecosystem functions such as regulation, support, and supply.

At present, the commonly used quantitative assessment methods of soil health mainly include 7 quantitative analyses:

1) The multivariate index Kriging method: The Kriging method can be carried out by integrating an unlimited number of individual soil quality indicators determined by experiments into one soil quality index according to specific standards and through multivariate index conversion.

2) The soil quality dynamics method: This method may include a soil quality dynamic function: $Q=f(q_i \ldots n)$, where Q is a soil quality and $q_i$ is a soil property.

3) The relative soil quality index method: This method result is conventionally obtained by comparing a soil quality index of a study area with a soil quality index under ideal conditions.

4) The principal component analysis: The principal component analysis is a statistical analytical method that recombines many relevant indices into a new set of unrelated multi-indices. The principal component analysis is the most widely used in the quantitative assessment of soil quality and can screen the variability of soil properties objectively and accurately.

5) Grey correlation analysis: This method can be carried out by judging the relational degree of the development trend of a grey process according to the similarity of geometric shapes of a series of curves, where the method has the characteristics of simple operation, reliable theory, and small calculation amount and the like, and is used in combination with a geographic information system (GIS).

6) The fuzzy mathematics comprehensive evaluation method: This method can be carried out by describing the gradual change and fuzziness of soil quality status changes using the degree of membership, to make the evaluation results more accurate and reliable, where the method not only uses the fuzzy characteristics in the soil quality assessment but also considers the joint influence of the evaluation factor index value, the evaluation factor weight and the interaction between the evaluation factors on the soil quality; therefore, the method can accurately and scientifically assess the soil quality status.

7) An artificial neural network model method: This method is a calculation method constructed on the basis of simulating the behavior characteristics of biological neural network.

Currently, the seven conventional methods described above may have the following main problems and deficiencies:

1) Soil scientists and ecologists have not yet reached an agreement on the concept of soil health. In different periods and fields, different researchers have different focuses on the definition of soil health. Therefore, soil health research is a long-term and dynamic development, which also shows the complexity and importance of soil health research.

2) There is no complete distinction between soil health and soil quality, and most researchers believe that the two are synonymous. In fact, health has all elements for the evaluation object, that is, the evaluation object will be unhealthy if a certain element is unhealthy. There is no meaning for health to soil itself, but meaning to the soil on which a certain organisms depend. In other words, soil health is targeted to different organisms and has a different meaning of health based on different living things that depend on the soil.

3) Due to the unclear connotation of soil health, the soil health assessment index systems and methods still follow the conventional soil quality assessment methods described above. However, conventional methods, and their respective assessment results cannot reflect the unhealthy elements for the individual soil, such that it is impossible to clarify the direction of soil cultivation. For crops on the soil, the health of the soil to a certain crop cannot be reflected, that is, the lack of specificity of the soil to the crop. Moreover, the assessment index systems and methods are also inconsistent, and may not be suitable for soil health assessment.

Accordingly, it is advantageous to establish a robust assessment index system and method for soil health to inform stakeholders about soil improvement or conservation.

SUMMARY

An objective of the present disclosure is to overcome the shortcomings of the prior art and provides a method for assessing soil health of cultivated land. The objective of the present disclosure is implemented by using the following technical solution: a method for assessing soil health of cultivated land, wherein the method includes the following steps:

Step 1 (S1): Soil sample collection: selecting 4-6 representative plots' soil to be sampled and investigated from plots with a highest yield in cultivated land to be subjected to health assessment as a control group; and selecting plots to be sampled and investigated from the cultivated land to be subjected to health assessment as an experimental group; where the plots with the highest yield are determined by visiting farmers or by querying local statistical reports;

Step 2 (S2): Indicator measurement: Step 2 may include measuring indicators of the control group and the experimental group separately, where the measuring indicators include a soil function index system, a soil nutrition index system, and a crop output index system. This step may also include an index value of the control group that is an index health value E, and an index value of the experimental group that is an index current value C;

The soil function index system includes one or more water and gas regulation indicators, one or more nutrition regulation indicators, and one or more comprehensive regulation indicators. In one aspect, the water and gas regulation indicator(s) may include a soil bulk density, field moisture capacity, and a withering coefficient. The nutrition regulation indicator(s) can include a cation exchange capacity (CEC), an organic matter content, and a soil carbon-nitrogen ratio (C/N). According to another aspect, the comprehensive regulation indicator may include a soil thickness value, a pH value, a microbial biomass value, a microbial main functional gene value, a microbial group, and soil enzyme activity information;

The soil nutrition index system can include macro-elements and trace elements. The macro-elements may include a soil total nitrogen value, total phosphorus information, total potassium information, available nitrogen information, available phosphorus information, available potassium information, a nitrogen-phosphorus ratio (N/P), and a nitrogen-potassium ratio (N/K). In another aspect, the trace element may include available zinc, available boron, and available molybdenum data.

The crop output index system includes a macro-view indicator and a micro-view indicator.

The macro-view indicators may include product output and income information.

The micro-view indicators can include product quality information.

According to one or more embodiments, the third step (S3) include a health assessment. This step can include performing a soil health assessment using a deviating degree of a ratio R that includes, for example, an index current value C/index health value E of a measured dual index from 1. That is, this step may include performing a health level assessment using a deviating degree of the soil function index $C_i/E_i=R_i$, the soil nutrition index $C_j/E_j=R_j$ and the crop output index $C_k/E_k=R_k$ from 1; where an assessment relationship between deviates a degree of the ratio R from 1 and the health level of the index, and the number of different health level indicators and the overall health level of the soil. Example results are shown in Table 1:

TABLE 1

Assessment relationship between index status and health level.

| The deviating degree of index ratio ($R_i$, $R_j$, and $R_k$) from "1" and index health level grading | | Number of different health level indicators and overall soil health level grading | |
| --- | --- | --- | --- |
| Degree | Grading, health level | Number of indicators, q = m + n + p | Health level |
| 0 ≤ \|$R_i$ or $R_j$ or $R_k$ − 1\| < 0.2 | 0, healthy | > or =80% indicators meeting "0" level | Healthy |
| 0.2 ≤ \|$R_i$ or $R_j$ or $R_k$ − 1\| < 0.4 | 1, sub-healthy | > or =20% indicators meeting "1" level | Sub-healthy |
| 0.4 ≤ \|$R_i$ or $R_j$ or $R_k$ − 1\| < 0.6 | 2, weak | > or =20% indicators meeting "2" level | Weak |
| 0.6 ≤ \|$R_i$ or $R_j$ or $R_k$ − 1\| | 3, disabled | > or =20% indicators meeting "3" level | Disabled |

In Table 1, i is 1, 2, 3 ... m, j is 1, 2, 3 ... n, and k is 1, 2, 3 ... p.

In the above ratio, if the numerator is smaller than the denominator, the numerator is divided by the minimum of the denominator. Conversely, if the numerator is greater than the denominator, the numerator is divided by the maximum of the denominator.

In one or more embodiments, the soil sample collection in S1 may be performed before fertilization or after harvesting.

In one or more embodiments, the soil sample collection in S1 may be performed in three layers: in a cultivated layer, soil in 0-10 cm depth and soil in 11-20 cm depth are separately collected, and in a non-cultivated layer, soil in 21-40 cm depth or 21-60 cm depth is collected.

In one or more embodiments, the microbial main functional gene, the microbial group, and the product quality in S2 may be calculated after value assignment, and a specific assignment method may be: the microbial main functional gene and the microbial group are separately assigned values of 1, 0.8, 0.6, and 0.4 according to a large quantity, medium quantity, small quantity and extremely small quantity; and the product quality is separately assigned values of 1, 0.8, 0.6 and 0.4 according to good quality, fair quality, poor quality, and extremely poor quality.

The present disclosure further provides a use of the method in soil health assessment, restoration, and conservation.

The present disclosure may have the following advantages:

(1) In the present disclosure the soil health is defined as soils having excellent functions that fully satisfy crop growth, sufficient and coordinated soil nutrition, and the ability to produce high-yield and high-quality products.

(2) The present disclosure adopts "three sets of dual index assessment systems", that is, an index system for a current soil function and a healthy soil function required by crops, which is a diagnostic index system for soil functional health as well as an index system mainly considered by soil experts; an index system for current soil nutrition (including coordination) and healthy soil nutrition required by crops, which is a diagnostic index system for soil nutritional health as well as an index system mainly considered by soil managers; and an index system for a current crop output (including production quality) of cultivated land and a crop output expected by cultivated land users or owners, which is a diagnostic index system for soil service health as well as an index system mainly considered by owners or users. The index system solves the shortcomings of existing indices that the existing soil health assessment index system mainly reflects the indicators of soil physics, chemistry, and biology, and has no hierarchy and applicability.

(3) The present disclosure assesses the health level by dividing the index current value (C) by the index health value (E) to obtain a ratio and using the deviating degree of the ratio from "1" and the number of indicators of the ratio. A farther deviation from "1" and more indicators that deviate from "1" lead to a lower health level, and a greater deviation from "1" refers to an unhealthy soil factor. The method is simple, and the assessment result can directly determine the indicators or factors that can be used for guiding soil improvement and conservation.

DETAILED DESCRIPTION OF THE EMBODIMENTS

The present disclosure is further described below in conjunction with the accompanying drawings and specific examples, but the protection scope of the present disclosure is not limited thereto.

Example 1

Experimental field: a type of purple soil in Yanting, Sichuan China.

Figure 1:
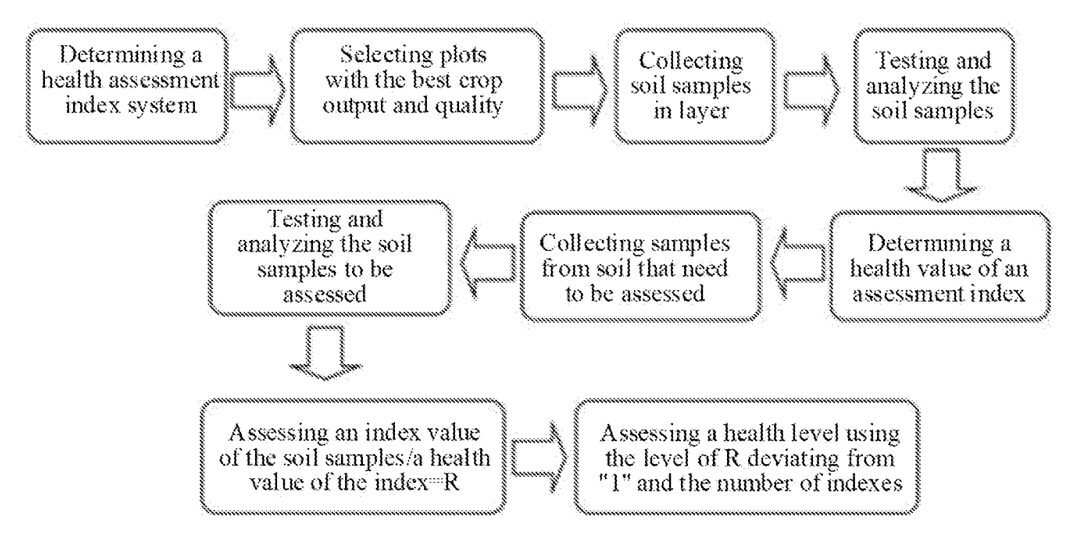
FIG. 1 is a flowchart for an assessment method of the present disclosure.

Experimental method: as shown in FIG. 1, a method for assessing soil health of cultivated land may include the following steps:

S1. Soil sample collection: 4-6 representative plots' soil to be sampled and investigated from plots with the highest yield in cultivated land to be subjected to health assessment were selected as a control group; and plots to be sampled and investigated from the cultivated land to be subjected to health assessment were selected as an experimental group; while the soil sample collection was performed before fertilization or after harvesting, as well as the plots with the highest yield were determined by visiting farmers.

In order to accurately diagnose the characteristics of the nutrition and function of healthy soil, a soil collection was performed in three layers according to the habit of surface application and intermittent application of fertilization: in a cultivated layer, soil in 0-10 cm depth and soil in 11-20 cm depth were separately collected, and in a non-cultivated layer, soil in 21-40 cm depth or 21-60 cm depth was collected.

Soil sampling types can include: (1) A soil composite sample: 1 soil composite sample may be collected per layer at each sampling point (plot), and each composite sample included 5-8 spot samples.

(2) A soil core sample: This step may include sampling undisturbed soil by a core (e.g., a sample volume of 100 cm$^3$). This step may further include collecting 3-5 samples per layer at each sampling point (plot).

(3) A soil microbial sample: This step may be similar the above method of collecting the composite sample, but with the additional step of refrigerating the sample.

S2. Index measurement: This step may include measuring the indicators of the control group and the experimental group separately, where the measured indicators include the soil function index system, the soil nutrition index system, and the crop output index system. An index value of the control group can include an index health value E, and an index value of the experimental group having an index current value C.

According to one embodiment, the soil function index system may include a water and gas regulation indicator, a nutrition regulation indicator, and a comprehensive regulation indicator.

The water and gas regulation indicator may include a soil bulk density, a field moisture capacity, and a withering coefficient.

The nutrition regulation indicator can include a cation exchange capacity, an organic matter content, and a soil carbon-nitrogen ratio. In one aspect, the comprehensive regulation indicator may include soil thickness, soil pH, microbial biomass, a microbial main functional gene, a microbial group, and a soil enzyme activity.

The soil nutrition index system includes macro elements and trace elements information.

The macro elements includes information including soil total nitrogen, total phosphorus, total potassium, available nitrogen, available phosphorus, available potassium, nitrogen-phosphorus ratio, and nitrogen-potassium ratio.

The trace elements can include available zinc, available boron, and available molybdenum data.

The crop output index system includes a macro-view indicator and a micro-view indicator.

The macro-view indicator may include soil output and income.

The micro-view indicator may include product quality.

Specific indoor analysis items and methods were as follows:

(1) Determining the soil function index (i), can include sub-steps A, B, and C as described below:

A. According to one embodiment, the soil bulk density, field moisture capacity, and wither coefficient may be determined by pressure plate extractor using the core samples.

B. According to another aspect of the present disclosure, the soil organic matter, cation exchange capacity (CEC), organic matter, carbon-nitrogen ratio (C/N), soil thickness, soil pH, and soil enzyme activity may be determined by conventional analysis methods. One such method is described in the document by Liu Guangsong, *Soil Physical and Chemical Analysis & Description of Soil Profiles*. (Beijing, Standards Press of China, 1996), which is incorporated herein by reference.

C. According to another embodiment, the soil microbial biomass, microbial main functional gene, and the microbial group are determined using high-throughput sequencing methods described by Wang Xingchun, Yang Zhirong, Wang Min, Li Wei, and Li Shengcai. in the document titled, HIGH-THROUGHPUT SEQUENCING TECHNOLOGY AND ITS APPLICATION (*China Biotechnology*, 2012, 32 (01): 109-114), which is incorporated herein by reference.

(2) Method for determining the soil nutrition index (j), which may include element D:

D. According to one or more embodiments, the total and effective amount of soil macro and trace elements may be determined by conventional analysis methods such as those described by Liu Guangsong in the publication titled, *Soil Physical and Chemical Analysis & Description of Soil Profiles* (Beijing, Standards Press of China, 1996), which is incorporated herein by reference.

(3) Determining the crop output index (k): In some aspects, the output and income may be determined by field investigation and sales registration. In other aspects, the product quality may be determined by corresponding product quality determination method, as understood by those skilled in the art.

The microbial main functional gene, the microbial group, and the product quality are calculated after value assignment, and a specific assignment method may be as follows: the microbial main functional gene and the microbial group can be separately assigned values of 1, 0.8, 0.6, and 0.4 according to a large quantity, medium quantity, small quantity and extremely small quantity, respectively; The product quality was separately assigned values of 1, 0.8, 0.6 and 0.4 according to good quality, fair quality, poor quality, and extremely poor quality.

The determination and assignment results are shown in Table 2.

TABLE 2

Dual index table of the example

| "Three sets" (i, j, and k) index system | | | "Dual" (C-E) indicators | |
| --- | --- | --- | --- | --- |
| First-level indicators | Second-level indicators | Third-level indicators (i) | (Experimental group) index current value $C_i$ | (Control group) index health value $E_i$ |
| Function Index system (Indicators considered by experts) | Water and gas regulation | Bulk weight | 1.4 | 1.3 |
| | | Field moisture capacity | 0.3 | 0.4 |
| | | Wither coefficient | 0.2 | 0.15 |
| | Nutrient regulation | Cation exchange capacity (CEC) | 18 | 25 |
| | | Organic matter | 1.1 | 2.0 |
| | | Carbon-nitrogen ratio (C/N) | 15 | 20 |
| | Comprehensive regulation | Soil thickness | 80 | 100 |
| | | pH | 8 | 7 |
| | | Microbial biomass | 40 | 60 |
| | | Microbial main functional gene | 0.6 | 1 |
| | | Microbial group | 0.8 | 1 |
| | | Soil enzyme activity | 25 | 30 |
| First-level indicators | Second-level indicators | Third-level indicators (j) | Index current value $C_j$ | Index health value $E_j$ |
| Nutrition index system (Indicators considered by managers) | Macro element | Total nitrogen | 1.2 | 1.5 |
| | | Total phosphorus | 0.6 | 1.0 |
| | | Total potassium | 1.8 | 3.0 |
| | | Available nitrogen | 160 | 200 |
| | | Available phosphorus | 80 | 100 |
| | | Available potassium | 260 | 300 |
| | | Nitrogen-phosphorus ratio (N/P) | 1.2 | 1.5 |
| | | Nitrogen-potassium ratio (N/K) | 0.8 | 1.0 |
| | Trace element | Available zinc | 8 | 10 |
| | | Available boron | 5 | 10 |
| | | Available molybdenum | 5 | 10 |

TABLE 2-continued

Dual index table of the example

| First-level indicators | Second-level indicators | Third-level indicators (k) | Index current value $C_k$ | Index expected value $E_k$ |
|---|---|---|---|---|
| Output Index system (Indicators considered by owners or users) | Macro-view | Output | 400 | 500 |
| | | Income | 1500 | 2000 |
| | Micro-view | Product quality | 0.8 | 1 |

S3. Determining health assessment: According to one or more embodiments, a soil health assessment may be performed using a deviating degree of a ratio R i.e., the index current value C/index health value E of a measured dual index from 1. That is, a health level assessment is performed using deviating degree of the soil function index $C_i/E_i=R_i$, the soil nutrition index $C_j/E_j=R_j$ and the crop output index $C_k/E_k=R_k$ from 1.

In the above ratio, if the numerator is smaller than the denominator, the numerator may be divided by the minimum of the denominator. Conversely, if the numerator is greater than the denominator, the numerator may be divided by the maximum of the denominator.

The R-value of each indicator and the absolute value of deviation from "1" can be calculated from Table 2. The health level of each index according to Table 1 is shown in Table 3.

According to the health level of the indicators in the table, there are 4 health indicators, 17 sub-health indicators, and 6 weakness indicators, accounting for 15%, 63%, and 22% of the total indicators, respectively. Therefore, according to the grading standard of overall soil health (Table 1), the overall health of the soil is weakness in Example 1.

The foregoing description only provides preferred specific implementations of the present disclosure, and the protection scope of the present disclosure is not limited thereto. Any equivalent replacement or modification made according to the technical solution and inventive concept by a person skilled in the art within a technical scope of the present disclosure shall fall within the protection scope of the present disclosure.

TABLE 3

Assessment results of the example.

"Three sets" (i, j, and k) index system

| First-level indicators | Second-level indicators | Third-level indicators | R-value | $\|R_i$ or $R_j$ or $R_k - 1\|$ | Health level |
|---|---|---|---|---|---|
| Function Index system (Indicators considered by experts) | Water and gas regulation | Bulk weight | 1.08 | 0.08 | Sub-healthy |
| | | Field moisture capacity | 0.75 | 0.25 | Sub-healthy |
| | | Wither coefficient | 1.33 | 0.33 | Sub-healthy |
| | Nutrient regulation | Cation exchange capacity (CEC) | 0.72 | 0.28 | Weak |
| | | Organic matter | 0.55 | 0.45 | Sub-healthy |
| | | Carbon-nitrogen ratio (C/N) | 0.75 | 0.25 | Sub-healthy |
| | Comprehensive regulation | Soil thickness | 0.80 | 0.20 | Healthy |
| | | pH | 1.14 | 0.14 | Sub-healthy |
| | | Microbial biomass | 0.67 | 0.33 | Weak |
| | | Microbial main functional gene | 0.60 | 0.40 | Sub-healthy |
| | | Microbial group | 0.80 | 0.20 | Sub-healthy |
| | | Soil enzyme activity | 0.83 | 0.17 | Healthy |
| Nutrient Index system (Indicators considered by managers) | Macro element | Total Nitrogen | 0.80 | 0.20 | Sub-healthy |
| | | Total Phosphorus | 0.60 | 0.40 | Weak |
| | | Total potassium | 0.60 | 0.40 | Weak |
| | | Available nitrogen | 0.80 | 0.20 | Sub-healthy |
| | | Available Phosphorus | 0.80 | 0.20 | Sub-healthy |
| | | Available potassium | 0.87 | 0.13 | Healthy |
| | | Nitrogen-phosphorus ratio (N/P) | 0.80 | 0.20 | Sub-healthy |
| | | Nitrogen-potassium ratio (N/K) | 0.80 | 0.20 | Sub-healthy |
| | Trace element | Available zinc | 0.80 | 0.20 | Sub-healthy |
| | | Available boron | 0.50 | 0.50 | Weak |
| | | Available molybdenum | 0.50 | 0.50 | Weak |
| Output Index system (Indicators considered by owners or users) | Macro-view | Output | 0.80 | 0.20 | Sub-healthy |
| | | Income | 0.75 | 0.25 | Sub-healthy |
| | Micro-view | Product quality | 0.80 | 0.20 | Sub-healthy |

What is claimed is:

1. A method for assessing a soil health of cultivated land, comprising the following steps:
a soil sample collection step comprising:
selecting 4-6 representative plots of soil to be sampled and investigated from plots with a highest yield in cultivated land to be subjected to health assessment as a control group;
collecting a first cultivated layer of the soil to be sampled from the control group comprising sampled soil in a 0-10 cm depth;
collecting a second cultivated layer of the soil to be sampled from the control group comprising sampled soil in a 11-20 cm depth, wherein the first cultivated layer and the second cultivated layer are separately collected; and,
collecting a non-cultivated layer of the soil to be sampled from the control group comprising sampled soil in a 21-40 cm depth or 21-60 cm depth; and,
selecting plots to be sampled and investigated from the cultivated land to be subjected to health assessment as an experimental group;
collecting a first cultivated layer of the soil to be sampled from the experimental group comprising sampled soil in a 0-10 cm depth;
collecting a second cultivated layer of the soil to be sampled from the experimental group comprising soil in 11-20 cm depth, wherein the first cultivated layer and the second cultivated layer are separately collected; and,
collecting a non-cultivated layer of the soil to be sampled from the experimental group comprising soil in 21-40 cm depth or 21-60 cm depth;
an index measurement step adapted to guide soil improvement comprising:
measuring indicators of the control group and the experimental group separately, wherein the indicators comprise a soil function index system, a soil nutrition index system, and a crop output index system; and an index value of the control group is an index health value E, and an index value of the experimental group is an index current value C;
wherein the soil function index system comprises a water and gas regulation indicator, a nutrition regulation indicator, and a comprehensive regulation indicator;
wherein the water and gas regulation indicator comprises soil bulk density, field moisture capacity, and wilting coefficient;
wherein the nutrition regulation indicator comprises cation exchange capacity (CEC), organic matter content, and soil carbon-nitrogen ratio (C/N); and,
wherein the comprehensive regulation indicator comprises a soil thickness, pH, microbial biomass, microbial main functional gene, microbial group, and a soil enzyme activity;
the soil nutrition index system comprising macroelements and trace elements;
the macro element comprising soil total nitrogen, total phosphorus, total potassium, available nitrogen, available phosphorus, available potassium, a nitrogen-phosphorus ratio (N/P), and a nitrogen-potassium ratio (N/K);
the trace element comprising available zinc, available boron, and available molybdenum;
the crop output index system comprising a macro-view indicator and a micro-view indicator;
wherein the macro-view indicator comprises output and income; and,
the micro-view indicator comprises a product quality; and,
performing a soil health assessment using a deviating degree of a ratio R comprising an index current value C/index health value E of a measured dual index; and,
performing a health level assessment using a deviating degree of the soil function index, the soil function index Ci/Ei=Ri, the soil nutrition index Cj/Ej=Rj and the crop output index Ck/Ek=Rk;
wherein an assessment relationship between deviating degree of the ratio R from 1 and the health level of the index, and the number of different health level indicators and the overall health level of the soil according to the following table:

| The deviating degree of index ratio ($R_i$, $R_j$, and $R_k$) from "1" and index health level grading | | Number of different health level indicators and overall soil health level grading | |
| --- | --- | --- | --- |
| Degree | Grading, health level | Number of indicators, q = m + n + p | Health level |
| $0 \leq \mid R_i$ or $R_j$ or $R_k - 1 \mid < 0.2$ | 0, healthy | > or = 80% indicators meeting "0" level | Healthy |
| $0.2 \leq \mid R_i$ or $R_j$ or $R_k - 1 \mid < 0.4$ | 1, sub-healthy | > or = 20% indicators meeting "1" level | Sub-healthy |
| $0.4 \leq \mid R_i$ or $R_j$ or $R_k - 1 \mid < 0.6$ | 2, weak | > or =20% indicators meeting "2" level | Weak |
| $0.6 \leq \mid R_i$ or $R_j$ or $R_k - 1 \mid$ | 3, disabled | > or =20% indicators meeting "3" level | Disabled | wherein i is 1, 2, 3 . . . m, j is 1, 2, 3 . . . n, and k is 1, 2, 3 . . . p.

2. The method according to claim 1, wherein the soil sample collecting is performed before fertilization or after harvesting.

3. The method for assessing soil health of cultivated land according to claim 1, wherein the microbial main functional gene, the microbial group, and the product quality in the experimental group are calculated after value assignment, and a specific assignment method.

4. The method for assessing soil health according to claim 3, further comprising:
defining the microbial main functional gene and the microbial group separately assigned values of 1, 0.8, 0.6, and 0.4 according to a large quantity, medium quantity, small quantity and extremely small quantity, respectively; and
defining the product quality is separately assigned values of 1, 0.8, 0.6 and 0.4 according to good quality, fair quality, poor quality, and extremely poor quality, respectively.

5. A method for improving soil health of cultivated land, comprising:
sampling soil in a plurality control group comprising 4 to 6 representative plots having a high yield in a first cultivated layer of 0-10 cm depth, a second cultivated layer of 11-20 cm depth separately, and a non-cultivated layer of 21-40 cm depth or 21-60 cm depth;

sampling soil in an experimental group comprising one or more plots subject to soil health assessment in a first cultivated layer of 0-10 cm depth, a second cultivated layer of 11-20 cm depth separately, and a non-cultivated layer of 21-40 cm depth or 21-60 cm depth;

generating a measuring index adapted to guide soil improvement, comprising:

measuring indicators of the control group and the experimental group separately, wherein the indicators comprise:

a soil function index system;
a soil nutrition index system;
a crop output index system; and,
an index value of the control group comprising an index health value E; and,
an index value of the experimental group comprising an index current value C;
wherein the soil function index system comprises:
a water and gas regulation indicator, a nutrition regulation indicator, and a comprehensive regulation indicator;
wherein the water and gas regulation indicator comprises:
soil bulk density, field moisture capacity, and wither coefficient;
wherein the nutrition regulation indicator comprises:
cation exchange capacity (CEC), organic matter content, and soil carbon-nitrogen ratio (C/N); and
wherein the comprehensive regulation indicator comprises:
a soil thickness, pH, microbial biomass, microbial main functional gene, microbial group, and a soil enzyme activity;
wherein the comprehensive regulation indicator comprises:
the soil nutrition index system comprising macroelements and trace elements;
wherein the macro elements comprise:
soil total nitrogen, total phosphorus, total potassium, available nitrogen, available phosphorus, available potassium, a nitrogen-phosphorus ratio (N/P) and a nitrogen-potassium ratio (N/K);
wherein the trace element comprises available zinc, available boron, and available molybdenum;
wherein the crop output index system comprises a macro-view indicator and a micro-view indicator; and
wherein the macro-view indicator comprises output and income;
the micro-view indicator comprises a product quality;
performing a soil health assessment using a deviating degree of a ratio R comprising an index current value C/index health value E of a measured dual index;

performing a health level assessment using a deviating degree of the soil function index, the soil function index $C_i/E_i = R_i$, the soil nutrition index $C_j/E_j = R_j$ and the crop output index $C_k/E_k = R_k$;

wherein an assessment relationship between deviating degree of the ratio R from 1 and the health level of the index, and the number of different health level indicators and the overall health level of the soil according to the following table:

| The deviating degree of index ratio ($R_i$, $R_j$, and $R_k$) from "1" and index health level grading | | Number of different health level indicators and overall soil health level grading | |
|---|---|---|---|
| Degree | Grading, health level | Number of indicators, q = m + n + p | Health level |
| $0 \leq |R_i$ or $R_j$ or $R_k - 1| < 0.2$ | 0, healthy | > or =80% indicators meeting "0" level | Healthy |
| $0.2 \leq |R_i$ or $R_j$ or $R_k - 1| < 0.4$ | 1, sub-healthy | > or =20% indicators meeting "1" level | Sub-healthy |
| $0.4 \leq |R_i$ or $R_j$ or $R_k - 1| < 0.6$ | 2, weak | > or =20% indicators meeting "2" level | Weak |
| $0.6 \leq |R_i$ or $R_j$ or $R_k - 1|$ | 3, disabled | > or =20% indicators meeting "3" level | Disabled | wherein i is 1, 2, 3 . . . m, j is 1, 2, 3 . . . n, and k is 1, 2, 3 . . . p; and, improving soil health in the one or more subject plots based on the assessment relationship.

6. The method according to claim 5, wherein the soil sample collection in the control group is performed before fertilization or after harvesting.

7. The method according to claim 5, wherein the microbial main functional gene, the microbial group, and the product quality in the experimental group are calculated after value assignment, and a specific assignment method is as follows: the microbial main functional gene and the microbial group are separately assigned values of 1, 0.8, 0.6, and 0.4 according to a large quantity, medium quantity, small quantity and extremely small quantity; and the product quality is separately assigned values of 1, 0.8, 0.6 and 0.4 according to good quality, fair quality, poor quality, and extremely poor quality.

8. A method for conserving soil health of cultivated land, comprising:

sampling soil in a control group comprising 4 to 6 representative plots having a high yield in a first cultivated layer of 0-10 cm depth, and a second cultivated layer of 11-20 cm depth separately, and a non-cultivated layer of 21-40 cm depth or 21-60 cm depth;

sampling soil in an experimental group comprising one or more plots subject to soil health assessment in a first cultivated layer of 0-10 cm depth, and a second cultivated layer of 11-20 cm depth separately, and a non-cultivated layer of 21-40 cm depth or 21-60 cm depth;

generating a measuring index adapted to guide soil conservation, comprising:

measuring indicators of the control group and the experimental group separately, wherein the indicators comprise:

a soil function index system;
a soil nutrition index system;
a crop output index system; and,
an index value of the control group comprising an index health value E; and,
an index value of the experimental group comprising an index current value C;
wherein the soil function index system comprises:
a water and gas regulation indicator, a nutrition regulation indicator, and a comprehensive regulation indicator;

wherein the water and gas regulation indicator comprises:
soil bulk density, field moisture capacity, and wither coefficient;
wherein the nutrition regulation indicator comprises:
cation exchange capacity (CEC), organic matter content, and soil carbon-nitrogen ratio (C/N); and
wherein the comprehensive regulation indicator comprises:
a soil thickness, pH, microbial biomass, microbial main functional gene, microbial group, and a soil enzyme activity;
wherein the comprehensive regulation indicator comprises:
the soil nutrition index system comprising macroelements and trace elements;
wherein the macro element comprises:
soil total nitrogen, total phosphorus, total potassium, available nitrogen, available phosphorus, available potassium, a nitrogen-phosphorus ratio (N/P) and a nitrogen-potassium ratio (N/K);
wherein the trace element comprises available zinc, available boron, and available molybdenum;
wherein the crop output index system comprises a macro-view indicator and a micro-view indicator; and
wherein the macro-view indicator comprises output and income;
the micro-view indicator comprises a product quality;
performing a soil health assessment using a deviating degree of a ratio R comprising an index current value C/index health value E of a measured dual index;
performing a health level assessment using a deviating degree of the soil function index, the soil function index $C_i/E_i=R_i$, the soil nutrition index $C_j/E_j=R_j$ and the crop output index $C_k/E_k=R_k$;
wherein an assessment relationship between deviating degree of the ratio R from 1 and the health level of the index, and the number of different health level indicators and the overall health level of the soil according to the following table:

| The deviating degree of index ratio ($R_i$, $R_j$, and $R_k$) from "1" and index health level grading | | Number of different health level indicators and overall soil health level grading | |
| --- | --- | --- | --- |
| Degree | Grading, health level | Number of indicators, q = m + n + p | Health level |
| $0 \leq |R_i$ or $R_j$ or $R_k - 1| < 0.2$ | 0, healthy | > or =80% indicators meeting "0" level | Healthy |
| $0.2 \leq |R_i$ or $R_j$ or $R_k - 1| < 0.4$ | 1, sub-healthy | > or =20% indicators meeting "1" level | Sub-healthy |
| $0.4 \leq |R_i$ or $R_j$ or $R_k - 1| < 0.6$ | 2, weak | > or =20% indicators meeting "2" level | Weak |
| $0.6 \leq |R_i$ or $R_j$ or $R_k - 1|$ | 3, disabled | > or =20% indicators meeting "3" level | Disabled | wherein i is 1, 2, 3 . . . m, j is 1, 2, 3 . . . n, and k is 1, 2, 3 . . . p; and,
conserving soil health in the one or more subject plots based on the assessment relationship.

9. The method according to claim 8, wherein the soil sample collection in the control group is performed before fertilization or after harvesting.

10. The method according to claim 8, wherein the microbial main functional gene, the microbial group, and the product quality in the experimental group are calculated after value assignment, and a specific assignment method is as follows: the microbial main functional gene and the microbial group are separately assigned values of 1, 0.8, 0.6, and 0.4 according to a large quantity, medium quantity, small quantity and extremely small quantity; and the product quality is separately assigned values of 1, 0.8, 0.6 and 0.4 according to good quality, fair quality, poor quality, and extremely poor quality.

* * * * *